United States Patent [19]

Go et al.

[11] Patent Number: 5,056,527
[45] Date of Patent: Oct. 15, 1991

[54] APPARATUS FOR ANALYZING VITAL SIGNALS BASED UPON A FEATURE SELECTED FROM A PLURALITY OF VITAL SIGNAL FEATURES

[75] Inventors: Takafumi Go; Tadashi Fujii, both of Kanagawa, Japan

[73] Assignee: Terumo Kabushiki Kaisha, Japan

[21] Appl. No.: 557,766

[22] Filed: Jul. 26, 1990

[30] Foreign Application Priority Data

Aug. 3, 1989 [JP] Japan .................................. 1-202186

[51] Int. Cl.⁵ .............................................. A61N 9/04
[52] U.S. Cl. .................................................... 128/702
[58] Field of Search ............... 128/696, 702, 703, 704, 128/705, 708

[56] References Cited

U.S. PATENT DOCUMENTS

| | | | |
|---|---|---|---|
| 3,820,025 | 6/1974 | Lahr et al. | 128/708 |
| 3,824,990 | 7/1974 | Baule | 128/702 |
| 3,880,147 | 4/1975 | Gruenke et al. | 128/702 |
| 4,023,564 | 5/1977 | Valiquette et al. | 128/704 |
| 4,250,888 | 2/1981 | Grosskopf | 128/702 |
| 4,698,848 | 10/1987 | Buckley | 128/696 |

*Primary Examiner*—William E. Kamm
*Attorney, Agent, or Firm*—Beveridge, DeGrandi & Weilacher

[57] ABSTRACT

A vital signal measuring apparatus includes histogram forming device to prepare histograms of a plurality of feature values associated with vital signals, causes a feature value selecting device to select on the basis of a distribution of the histograms, a feature value having information most useful to a vital signal analysis thereby effect a vital signal analysis by an analizing device with considerations of the individual characteristics of subjects. Yet, when a histogram is prepared in a predetermined period of time, accurate judgement and analysis of normality and abnormality in response to changes in a person during a day or between respective examination days can be achieved, and abnormal signals can be easily selected to be stored in a memory.

15 Claims, 9 Drawing Sheets

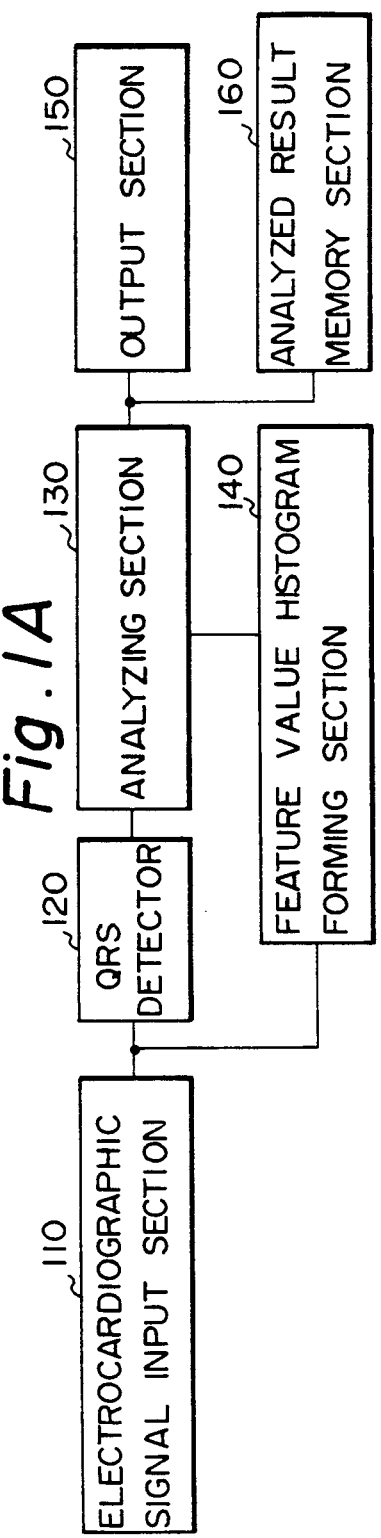
Fig. 1A
Fig. 1B
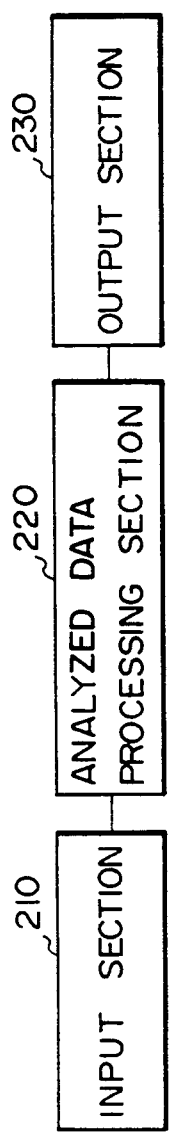
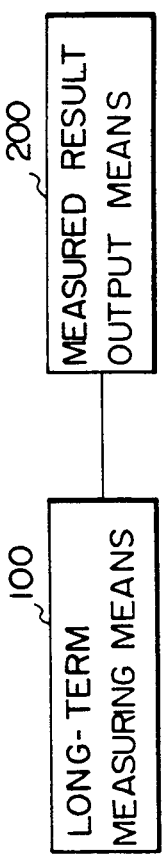
Fig. 2

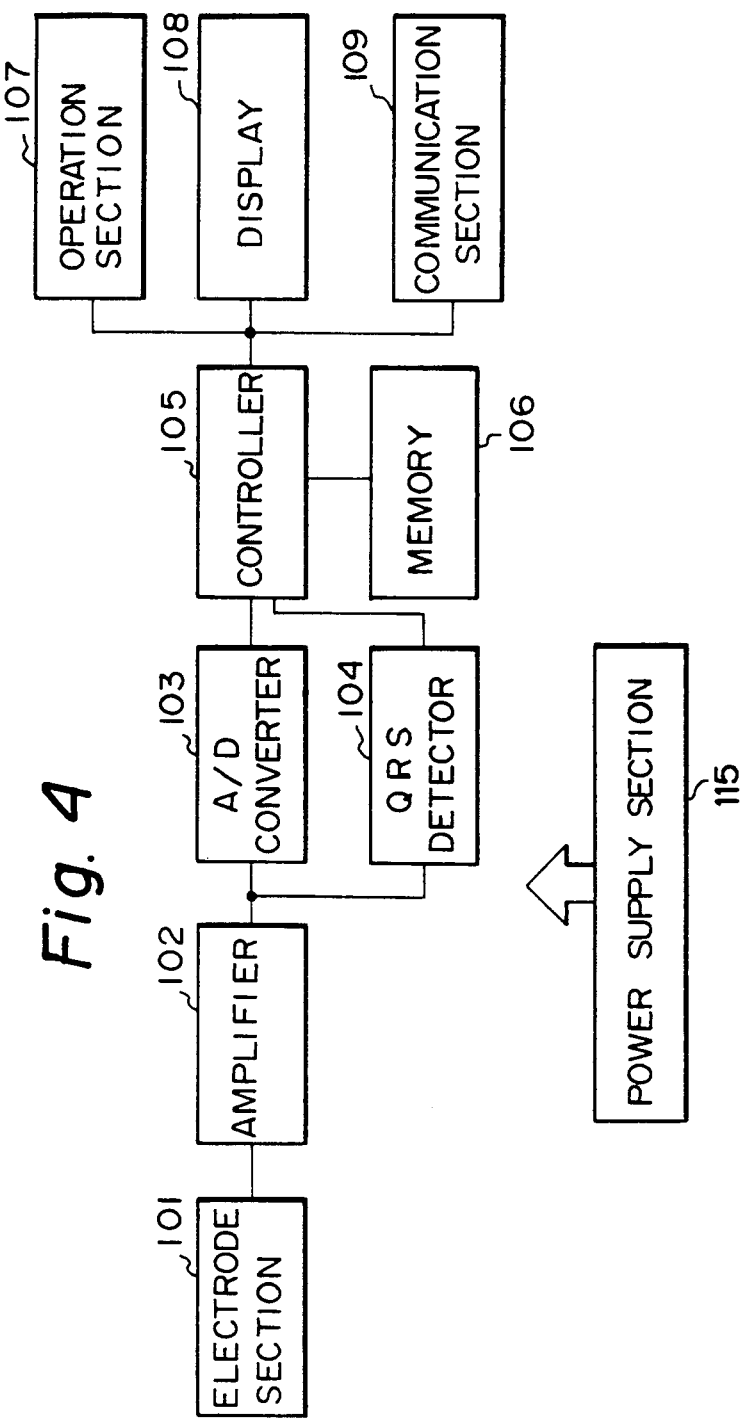
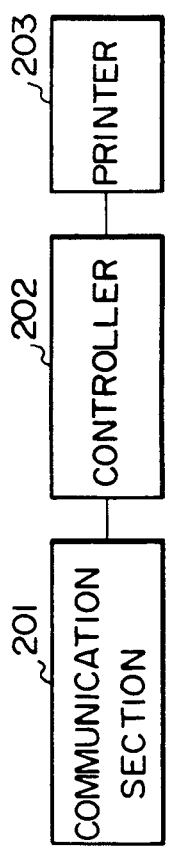

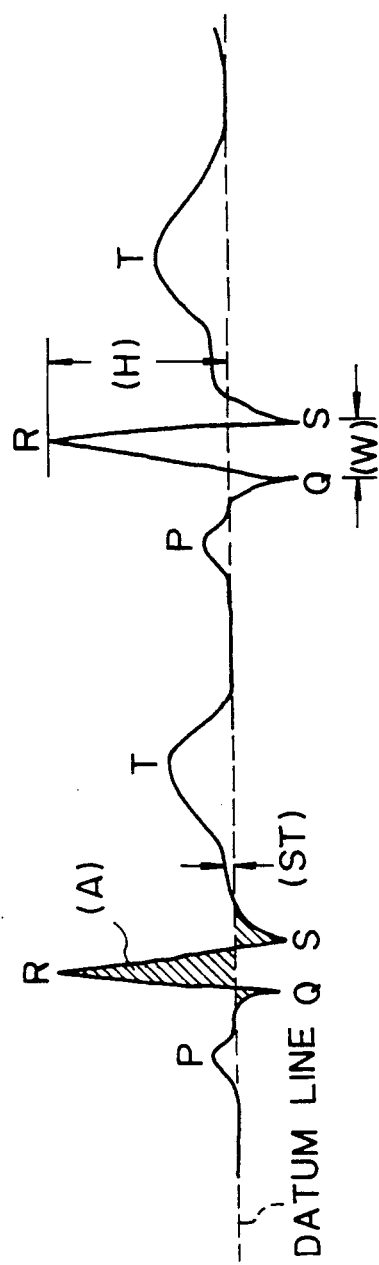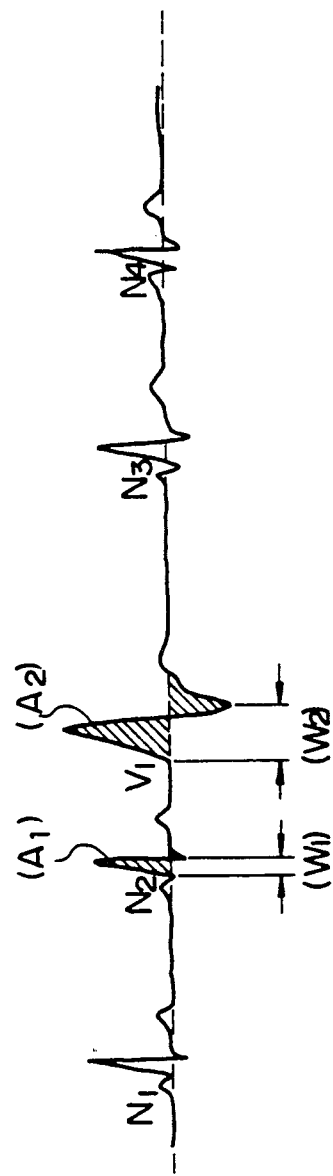

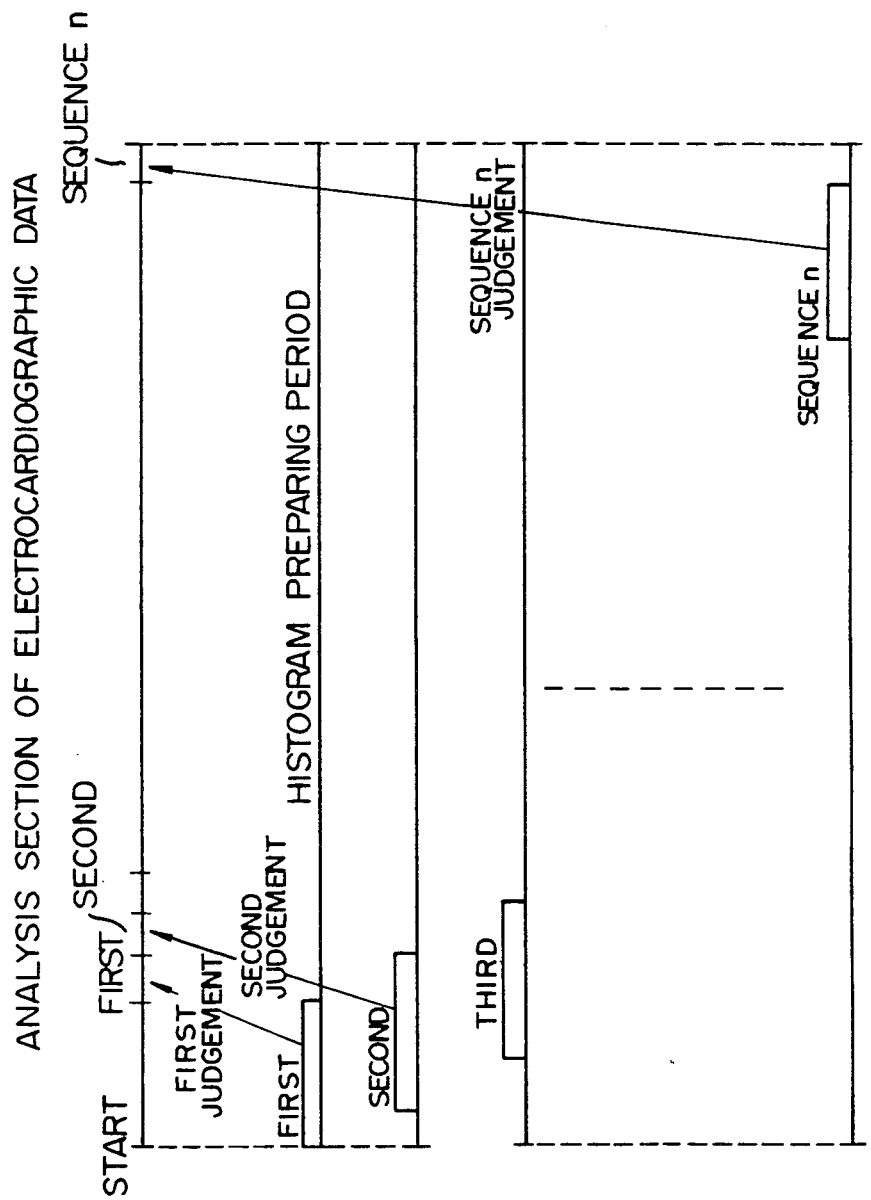

APPARATUS FOR ANALYZING VITAL SIGNALS BASED UPON A FEATURE SELECTED FROM A PLURALITY OF VITAL SIGNAL FEATURES

BACKGROUND OF THE INVENTION

1. Field of the Invention

The present invention relates to an apparatus for measuring a signal from a vital or a living body for a predetermined period of time, and in particular, to a living body signal measuring apparatus for analyzing a signal vital in a realtime fashion.

2. Description of the Prior Art

In the field of medical treatment, a clinical examination measuring, for example, an electrocardiogram and blood pressure is conducted as a daily job.

These examinations are ordinarily effected in quite a limited period of time in a medical care institution such as a clinic or a hospital under contro of a medical doctor or an examiner or inspector of the clinical institution. However, there exist diseases which cannot be detected in the examination conducted in such a limited period of time.

For example, in a case of a temporary disorder of the heart or an arrhythmia, there does not necessarily appear an abnormal waveform in the electrocardiogram. Since an interval between appearances of such an abnormal waveform is great in many cases, the probability of the detection of such a disorder of the heart in a short period of time is decreased; in consequence, it is difficult in many cases to conduct a determinant diagnosis through a examination conducted in a short period of time.

In this situation, for the detection of such diseases described above, there has been devised a method for measuring an electrocardiogram for a long period of time. According to this method, there is attained a long-term elctrocardiogram or so-called Holter electrocardiogram such that for an entire day or 24 hours in the daily life, a portable electrocardiograph is kept attached on a portion of the body of a person as a subject so as to collect and to record electrocardiographic waveforms on a magnetic tape. The magnetic tape is thereafter read by use of a magnetic tape playback apparatus so as to reproduce the electrocardiographic waveforms, which are observed by an inspector such as a medical doctor to detect an abnormality, thereby conducting a diagnosis of disease such as a fugitive affection of the heart.

The electrocardiographic waveforms recorded on a magnetic tape are reproduced at a high speed due to the great volume thereof. Consequently, the inspector, for example, a medical doctor is required to conduct the diagnosis by visually checking such a great amount of electrocardiographic waveforms reproduced at a high speed, which imposes a heavy load on the inspector.

As described above, in order to detect the arrhythmia which is a transitory disease and which appears at quite a rare occasion, the electrocardiographic waveforms collected in 24 hours are entirely reproduced so as to analyze the waveforms in a long period of time, which requires many unnecessary jobs and which decreases the efficiency of the overall examination.

In order to eliminate the irrationality above, there has been adopted a method in which a magnetic tape containing a great volume of recorded waveforms is reproduced at a high speed (for example, at a speed which is 60 or 120 times the ordinary playback speed) such that the waveforms are automatically analyzed according to a predetermined method by the apparatus so as to display only the portions thereof judged to be abnormal as a result of the analysis, thereby enabling an inspector to examine the abnormal portions. However, since the magnetic tape undergoes a high-speed playback operation and data items of the electrocardiographic waveforms are inputted to the objective apparatus at a high speed, when it is desired to analyze the waveforms by use of, for example, a microcomputer, there cannot be afforded a sufficient time for the analysis, namely, it is difficult at the present stage of the technology to increase the accuracy of the analysis.

In order to overcome such a difficulty, there has been recently employed a method in which while the electrocardiographic waveforms are being gathered for a long period of time, an analysis of the waveforms are automatically achieved at the same time, namely, in a realtime manner such that portions of the waveforms judged to be abnormal as a result of the analysis are stored in a storage, for example, on a magnetic tape or in an IC memory so as to thereafter display these abnormal waveforms and analysis results by means of a display equipment installed at a location of a medical doctor and to effect a print-out operation thereof if necessary, which enables the doctor to confirm the results. In this method, as compared with the method above, a sufficient time can be afforded to conduct the analysis (60 or 120 times), which improves the accuracy of the analysis.

In the realtime analysis of such a long-term measurement of electrocardiographic waveforms, all electrocardiographic waveforms appearing in 24 hours are not recorded, namely, there are stored only the waveforms judged to be abnormal as a result of the automatic analysis effected by the apparatus. In consequence, the waveforms judged to be normal by the automatic analysis are not stored, namely, even if there exists an abnormal waveform therein, the inspector cannot check such a waveform.

As described above, in the realtime analysis, it is quite important that any abnormal waveform can be detected; in addition, in order to minimize the examination job imposed on the inspector, it is also essential not to judge a normal waveform to be abnormal.

However, since the electrocardiographic waveforms include personal characteristics of the subject (differences in characteristcs associated with respective persons), if the normality and the abnormality are automatically judged depending on a predetermined reference value, it is likely to increase the ratio of errors in the judgement.

In other words, when using electrocardiographic waveforms, a QRS portion where a level of the waveform signal greatly varies is detected so as to compute values of an area of the QRS portion, an amplitude (height) thereof, and the time index (index of the width) thereof, thereby judging to determine the normality or the abnormality depending on whether or not these values exceed the respective predetermined threshold values. Due to the difference between the threshold values of the individual persons, with any threshold values set in a case where the realtime analysis is effected while continuously measuring the signal for 24 hours, there remains a fear that the error ratio is increased in the judgement.

For example, an attempt has been made to correctly detect with a high accuracy an extrasystole associated with the ventricule which is most problematical in the arrhythmia. In this case, the time index of the QRS portion (the index of the QRS width) is measured so as to determine the presence or absence of the extrasystole associated with the ventricule depending on whether or not the value of the measured index exceeds a predetermined threshold value. However, the threshold value as a boundary value between the normal value of the QRS index and the abnormal value thereof cannot be absolutely determined, namely, the value varies depending on the individual cases; moreover, it has been well known that, for a person, the value changes during a day or between respective examination days. Namely, even when the same value is obtained for the QRS index, the value may be normal or abnormal depending on the individual cases. In consequence, it is impossible to uniquely fix the threshold value to judge the normal and abnormal cases without causing any errors.

SUMMARY OF THE INVENTION

It is therefore an object of the present invention to remove the disadvantages of the prior art technology and to provide a long-period living body signal measuring apparatus capable of effecting a long-term vital signal measurement such that a long-term analysis is achieved with a high precision with considerations of the individual characteristics of measured waveforms.

According to the present invention, the vital signal measuring apparatus capable of effecting a measurement and an analysis of a vital signal of a subject to store the signal and reproduce the measured results includes a histogram forming means for forming a histogram of a plurality of feature values associated with a living body signal, a feature value selecting means for selecting on the basis of distribution of the prepared histogram the most useful information for a vital signal analysis, and an analizing means for analizing a vital signal by use of a selected feature value, wherein the analizing means determines whether the vital signal is normal or abnormal.

Further, according to the present invention, the histogram forming means forms a histogram in the unit of a predetermined period of time so as to design the histogram to record an abnormal vital signal in the latest period of time regarded as the predetermined period of time, the feature value selecting means selects a feature value having a shape showing the best condition of separation as a feature value having the most useful information for an analysis, the analizing means sets up a threshold value for determining whether the selected feature value is normal or abnormal to analize a vital signal on the basis of the threshold value.

BRIEF DESCRIPTION OF THE DRAWINGS

The objects and features of the present invention will become more apparent from the consideration of the following detailed description taken in conjunction with the accompanying drawings in which:

FIGS. 1A and 1B are block diagrams showing illustrative embodiments of a long-term measuring means and a measured result reproducing means included in the vital signal measuring apparatus of the present invention;

FIG. 2 is a block diagram showing the basic structure of the vital signal measuring apparatus of the present invention;

FIG. 4 is a block diagram showing a construction of hardware included in the portable electrocardiograph;

FIG. 5 is a block diagram showing a construction of hardware included in a printer;

FIG. 8 is a graph exemplifying feature values extracted from electrocardiographic waveforms;

FIG. 10 is a graph showing analysis steps;

FIG. 11 is a graph exemplifying normality and abnormality of electrocardiographic waveforms.

DESCRIPTION OF THE PREFERRED EMBODIMENTS

Referring now to the accompanying drawings, description will be given of embodiments of a vital signal measuring apparatus according to the present invention.

Figure 3A:
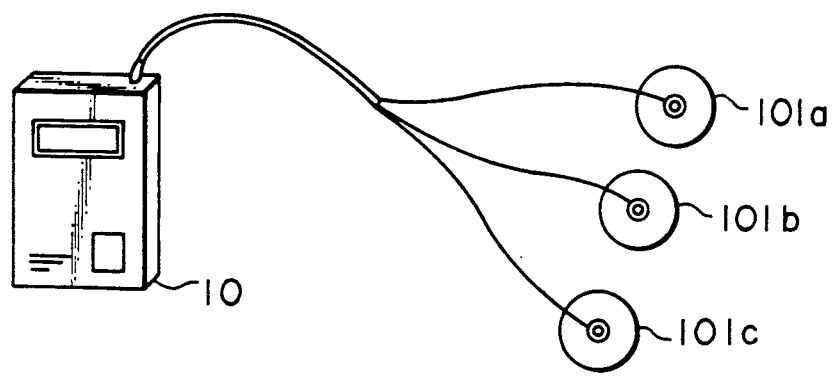
FIG. 3A is a front view of a portable electrocardiograph composing the vital signal measuring apparatus of the present invention.
Figures 3B, 3C:
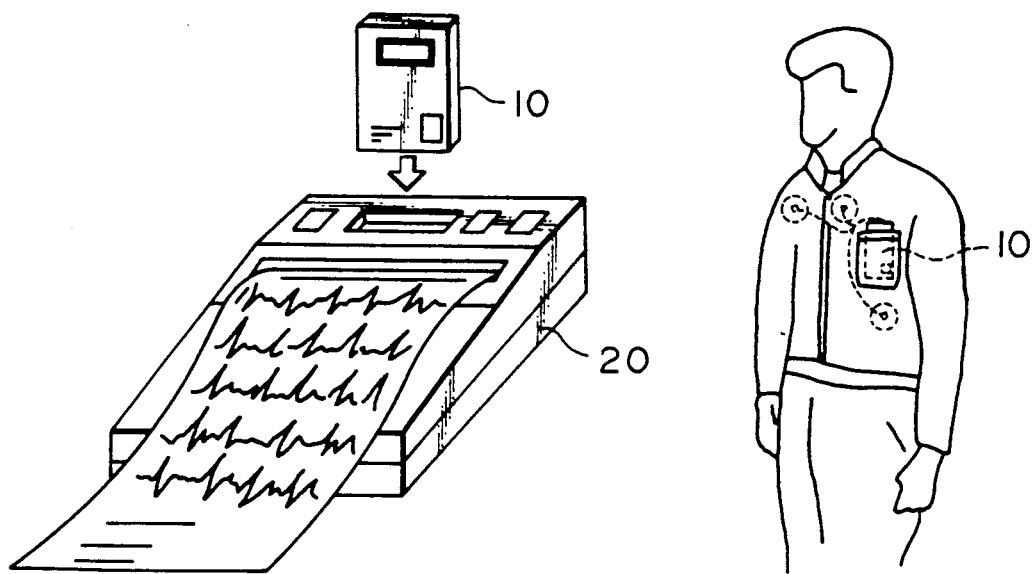
FIG. 3B is a perspective view of the portable electrocardiograph and a printer composing the vital signal measuring apparatus of the present invention.
FIG. 3C illustrates attachment of the portable electrocardiograph shown in FIG. 3A to a subject.

FIGS. 1A and 1B show an illustrative embodiment of the vital signal measuring apparatus according to the present invention, FIG. 2 shows the basic structure of the vital signal measuring apparatus according to the present invention, and FIGS. 3A, 3B, and 3C show a construction of hardware included in the vital signal measuring apparatus of the present invention, respectively. The measuring apparatus is concretely composed of a portable electrocardiograph 10 and a printer 20.

The basic structure of the vital signal measuring apparatus according to the present invention, as shown in FIG. 2, comprises a long-term measuring means 100 and a measured result reproducing means 200. The long-term measuring means 100 is a long-term electrocardiographic measuring apparatus, such as the portable electrocardiagraph 10, for example, to be attached on a person as a subject, as shown in FIGS. 3A and 3B. The portable electrocardiograph 10 which is carried with a subject as shown in FIG. 3C measures, while measuring electrocardiographic waveforms of the subject for a certain period of time as long as 24 hours, for example, feature values of the electrocardiographic waveforms for respective portions of the measured electrocardiographic waveforms, then analyzes the electrocardioghraphic waveforms to determine whether the electrocardiographic waveforms are normal or abnormal, and records the waveforms judged to be abnormal. The measured result reproducing means 200 is, for example, the printer 20 connected to the portable electrocardiograph 10 as shown in FIG. 3B. The printer 20 is, after the completion of a long-term measurement by the portable electrocardiograph 10, brought into connection with the portable electrocardiograph 10 to develop a result of the analysis and judgement, thereby a medical doctor or a clinical examiner conducts a clinical check and diagnosis.

FIG. 1A exemplifies a functional block configuration of the long-term measuring means 100, and FIG. 1B exemplifies a functional block configuration of the measured result reproducing means 200.

In the long-term measuring means 100 shown in FIG. 1A, there are an electrocardiographic signal input section 110 to which electrocardiographic signals from a subject are transmitted and a QRS detecting section 120 which detects a QRS portion of an electrocardiographic signal sent from the electrocardiographic signal input section 110. A feature value histogram forming part 140 forms a histogram, according to electrocardiographic signals sent from the electrocardiographic signal input section 110, of various kinds of feature values for the electrocardiographic signals. An analyzing section 130 uses, for electrocardiographic waveforms from which the QRS portion has been detected in the QRS detecting section 120, various kinds of histograms of feature values prepared by the feature value histogram forming section 140 to determine whether the electrocardiographic waveforms are normal or abnormal. An analyzed result recording section 160 records as the result of judgement on electrocardiographic waveforms, portions of the waveforms judged to be abnormal, portions of the waveforms in the vicinity of the abnormal waveforms, and appearing time of such abnormal waveforms. An output section 150 is connected to the printer 20 mainly for reproducing a result of the analysis on the printer 20.

In the measured result reproducing means 200 shown in FIG. 1B, an input secton 210 connected to the output section 150 of the portable electrocardiograph 10 is sent analyzed data from the portable electrocardiograph 10. An output section 230 displays and prints out the analyzed data sent from the input section 210 through an analyzed data processing section 220.

FIG. 4 is a block diagram showing hardware included in the portable electrocardiograph 10. FIG. 5 is a block diagram showing hardware included in the printer 20.

In the portable electrocardigraph 10 shown in FIG. 4, there is an electrode section 101 composed of a plurality of electrocardiographic electrodes 101a, 101b and 101c as shown in FIGS. 3A and 3C. The required number of electrodes is to be determined depending on an induction method. An amplifier 102 connected to the electrode section 101 amplifies electrocardiographic signals of a subject sent thereto from the electrode section 101. An A/D converter 103 converts the electrocardiographic signals amplified by the amplifier 102 into digital signals. A QRS detector 104 detects a QRS portion of electrocardiographic signals. A controller 105, by using a control program and an electrocardiographic signal analysis program incorporated therein, analyzes digital electrocardiographic signals sent from the A/D converter 103 to store the analyzed result in a memory 106. A display 108 and a communication section 109 are components composing the output section 150 shown in FIG. 1A. An operation section 107 is composed of a start button for starting electrocardiographic measurement and an event marker switch to be pressed by a subject when the subject is aware of any abnormality. A power supply section 115 composed of dry cells supplies electricity to all circuits included in the apparatus and holds a necessary capacitance required for the portable electrocardiograph 10 to carry out an analysis and a measurement of electrocardiographic signals for 24 hours or a longer period of time.

In the printer 20 shown in FIG. 5, a communication section 201 connected to the communication section 109 shown in FIG. 4 receives the analyzed result read out from the memory 106 of the portable electrocardiograph 10. A controller 202, when the analyzed result is transmitted thereto from the portable electrocardiograph 10 over the communication section 109, prepares the analyzed result in a prescribed output form. The analized result is then printed out by a printer 203.

Next, the procedure and operations of the vital signal measuring apparatus of the present invention will be described hereafter.

Figure 6:
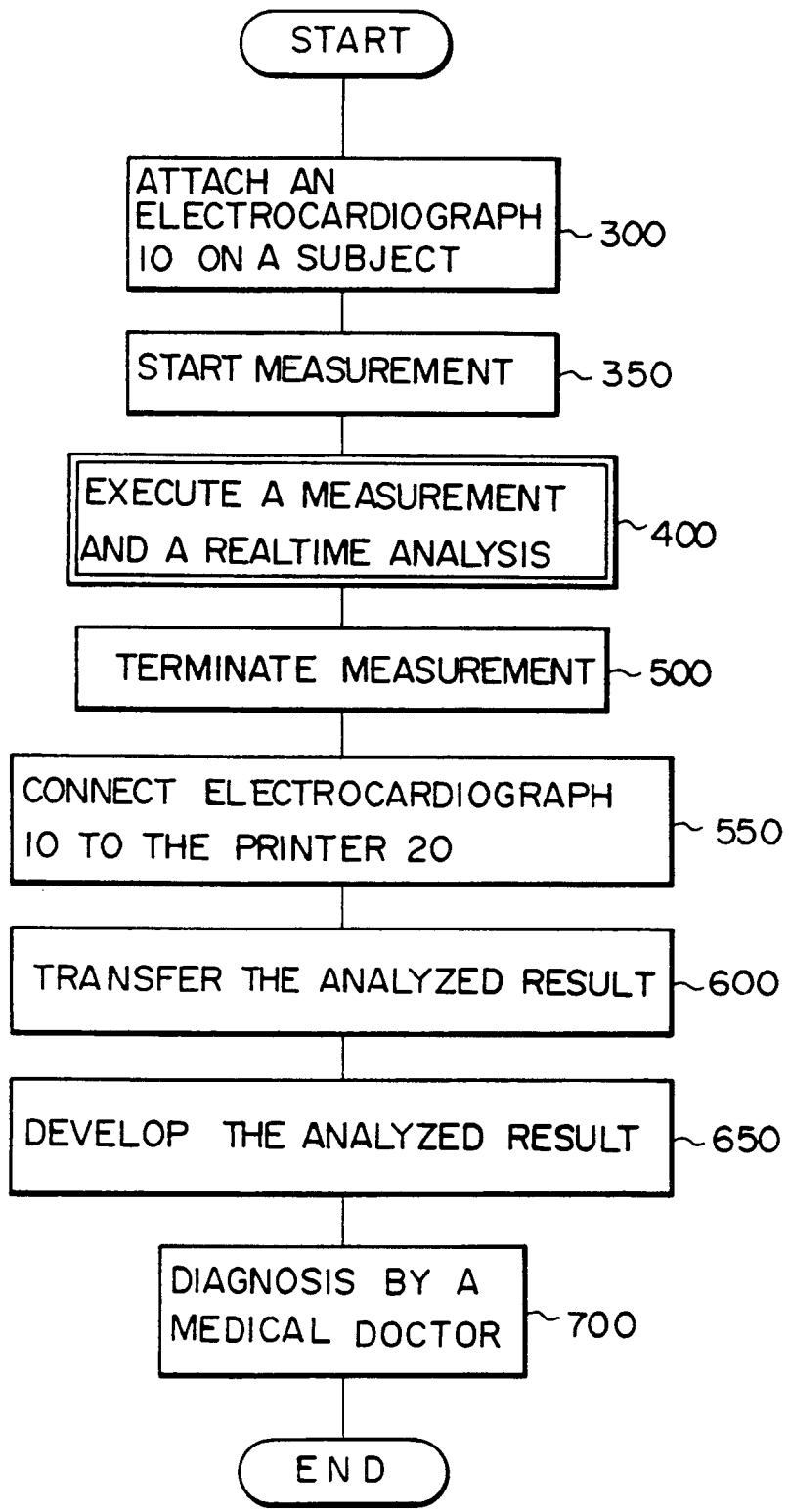
FIG. 6 is flowchart generally explaining procedure and operations of the vital signal measuring apparatus of the present invention.

FIG. 6 is a procedural flowchart explaining the procedure and operations of the vital signal measuring apparatus according to the present invention. To begin with, the portable electrocardiograph 10 is attached on the body of a subject by a medical doctor or a clinical examiner. Electrocardiographic electrodes of the electrode section 101 of the portable electrocardiograph 10, after an induction method is decided, are fixed on predetermined portions of the subject body, while the portable electrocardiograph 10 itself is kept attached on the subject (step 300).

The subject or the clinical examiner, after visually checking the display 108 on the portable electrocardiograph 10 to confirm that predetermined conditions have been satisfied, presses a start button for measurement. The predetermined conditions stated herein include matters that the voltage of dry cells has not decreased and that electrocardiographic signals have been received by the electrodes attached to the subject, for example. A judgement of whether or not those conditions have been satisfied is made in the controller 105. If not satisfied, a notice to this effect as an alarm is displayed on the display 108 (step 350).

When the start button for measurement is pressed, the portable electrocardiograph 10 carries out measurement of electrocardiographic signals of the subject in the daily life and analizes thereof in a realtime manner (step 400). After the completion of measurement for a predetermined period of time, for example, 24 hours, that effect is displayed on the display 108 (step 500). When the subject, after confirming the display, removes the electrodes from the body, the portable electrocardiograph 10 becomes in a state of measurement ended.

When the subject, after the completion of measurement, brings the portable electrocardiograph 10 back to the medical doctor again, the medical doctor connects the portable electrocardiograph 10 to the printer 20 (step 550).

Between the portable electrocardiograph 10 and the printer 20, a result of the analysis recorded in the memory 106 is transferred over the communication parts 109 and 201 to the control part 202 of the printer 20 (step 600).

The printer 20, after the completion of transferring the result of the analysis, prints the result of the analysis out of the printer section 203 in a prescribed form (step 650).

The medical doctor, after the analyzed result is printed out of the printer section 203 in a prescribed form, conducts a diagnosis on the basis of the printed result (step 700). Here, all the steps terminate.

Then, a measurement and a real time analysis in the step 400 will be elucidated hereafter.

Figure 7:
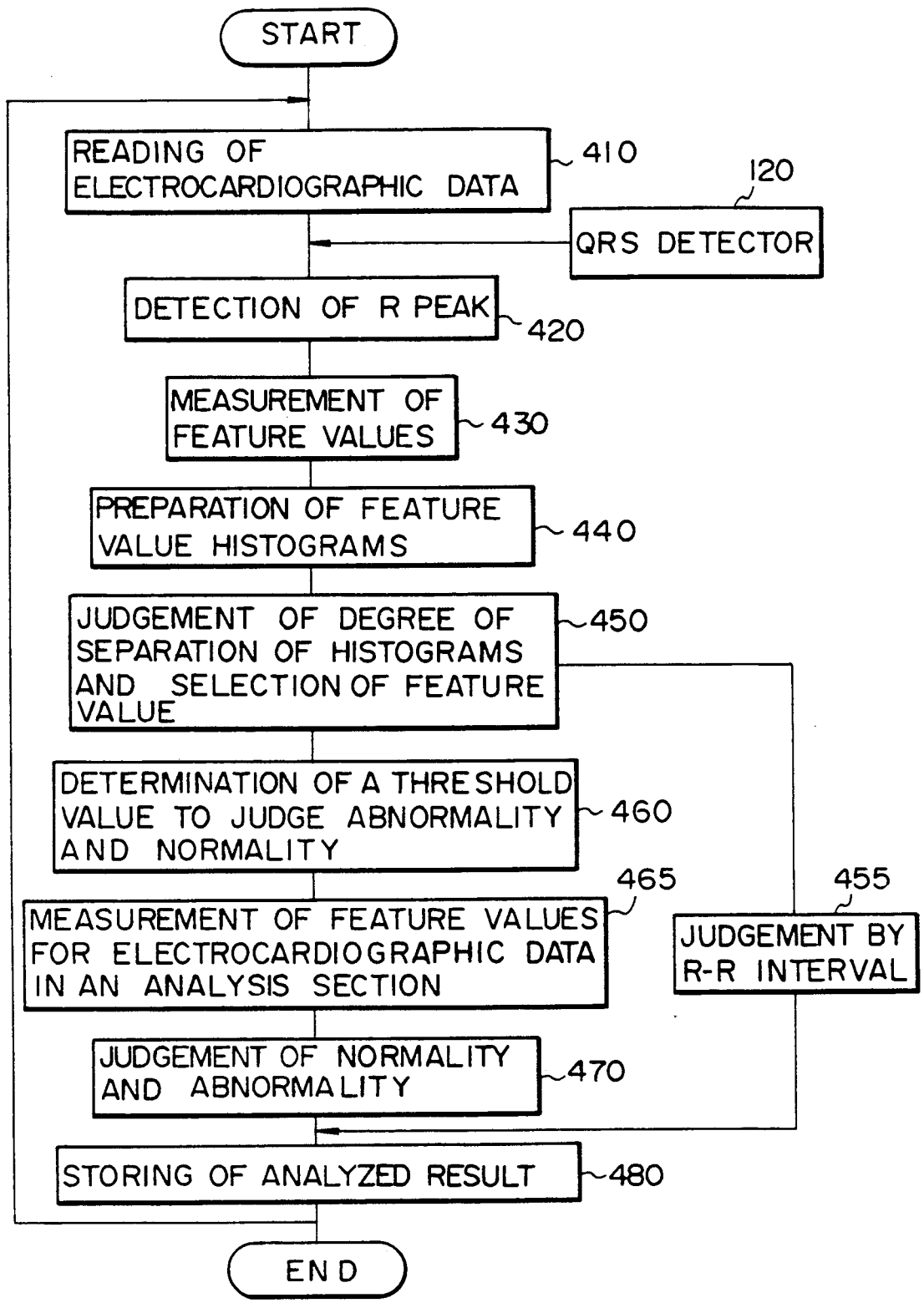
FIG. 7 is a flowchart showing a flow of measurement and realtime analysis.

FIG. 7 shows a flow of a measurement and a real time analysis, FIG. 8 exemplifies feature values extracted from electrocardiographic waveforms, FIG. 9 exemplifies histograms having a typical distribution, and FIG. 10 shows a time chart for explaining the entire processing flow, respectively.

In the process of e measurement and a real time analysis, electrocardiographic data (electrocardiographic signals) for a first predetermined period of time (for a unit period of time) are first read in the controller 105 (step 410). The R wave peak detection is carried out on the basis of signals detected by the QRS detector 104. In concrete, an analogical process, such as a combination method of band-pass filter process for efficiently extracting QRS waveforms as well-known and a detection process of a maximum value for waveforms to be processed, is used for the R wave peak detection.

In any case, the R wave peak which will be a basis for an electrocardiographic waveform analysis is detected in the step 420. Further, all of the R wave peak detection may be digitally processed within the controller 105. Continuously, to carry out an electrocardiographic analysis, a measurement of feature values for the electrocardiographic data that have been supplied is performed (step 430).

A feature value is datum which is the basis for determining whether an electrocardiographic waveform is normal or abnormal, such as an area A of the QRS portion, height H of the R wave peak, width W of the QRS portion, or a ST deflection ST, etc.

For a plurality of the feature values measured in the step 430, respective histograms are prepared (step 440).

For the respective histograms prepared in the step 440, the shape, namely, the distributing state of the feature values is analized. Then, in each histogram two mountain-shaped distributions are indicated on the basis of the distributing state, and yet, as shown in FIG. 9A, a feature value for a histogram having two mountain-shaped distributions clearly separated is detected (step 450).

Figure 9A:
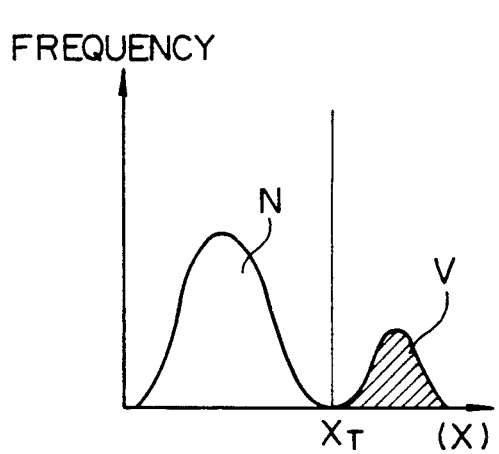
FIGS. 9A, 9B, and 9C are graphs exemplifying histograms having a typical distribution.

Then, by using the feature value selected in the steps 450, based on the two chevron-shaped distributions a threshold value, such as XT shown in FIG. 9A, is fixed (step 460).

Here, a feature value for electrocardiographic data in a first analysis section is measured (step 465).

Subsequently, by using the threshold value fixed in the step 460, for electrocardiographic data obtained in the first analysis section after the first predetermined period of time a judgement is made to determine whether the electrocardiographic data thereof are normal or abnormal (step 470).

Next, the electrocardiographic waveforms judged to be abnormal in the step 470, the waveforms before and after the abnormal waveforms, and appearing time of the abnormal waveforms are analyzed and the result from the analysis result is stored in the memory 106 (step 480).

Figure 9B:
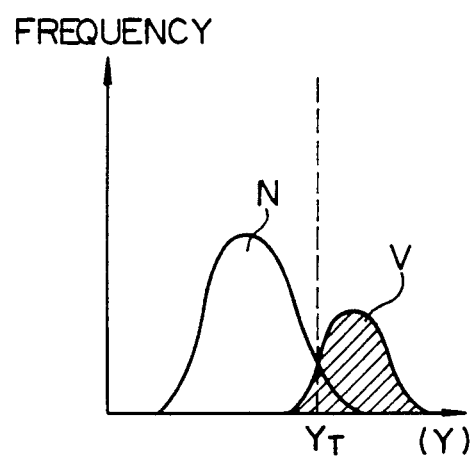
Figure 9C:
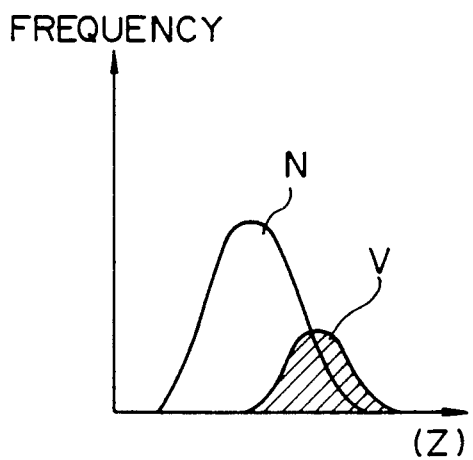

In the analysis described above, as an exceptional process, when a histogram for all the feature values indicates a distribution having an undesirable degree of separation, such as one shown in FIG. 9C or a single mountain-shaped distribution, the separation degree of the histogram in the step 450 cannot be judged. Therefore, processing proceeds to the step 455. In this occasion, a judgement is made in an R—R interval generally used.

In other words, for a predetermined pulse rate a moving average in the R—R interval is calculated and that which is below a predetermined percent of the moving average in the R—R interval is judged to be an abnormal waveform (an arrhythmia).

As described above, when the analysis of the electrocardiographic data in the first predetermined analysis section terminates, the same processing is repeated from the step 410 to execute preparation of a histogram in a second predetermined unit period of time, determination of a threshold value, and an analysis of electrocardiographic data in a second predetermined analysis section. The entire processing flow is illustrated in a timing chart shown in FIG. 10.

As shown in FIG. 10, the vital signal measuring apparatus of the present invention is characterized in that without using the already completed histogram and the analyzed result in the first predetermined unit period of time to prepare a histogram in the second predetermined unit period of time, a histogram in the second predetermined unit period of time is newly prepared on the basis of electrocardiographic data obtained in the second predetermined unit period of time to execute an analysis of electrocardiographic data in the second analysis section after the second predetermined unit period of time. In particular, to cope with variation and other change in a day a histogram is always updated for recognizing and selecting during that updating period a feature value having a high degree of separation at every time of updating to execute an analysis in predetermined analysis sections after the updating period. It is a matter of course that as a histogram is always updated, a threshold value is also updated in every unit period of time.

Next, a judgement to determine whether electrocardiographic waveforms are normal or abnormal and setting of a threshold value will be elucidated hereafter.

Figure 12A:
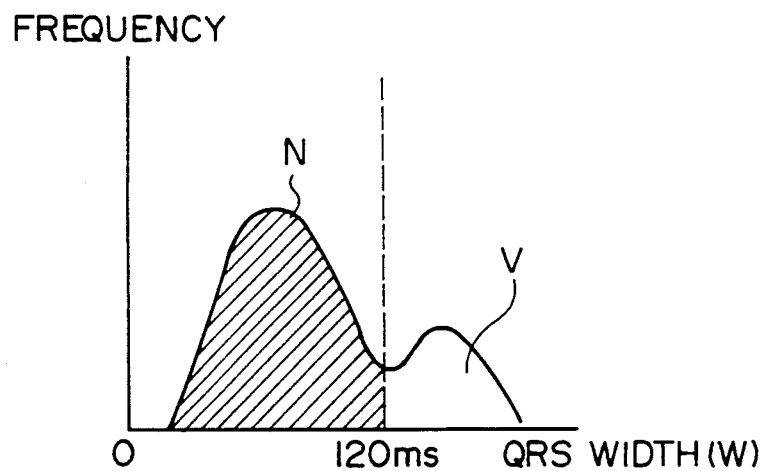
FIGS. 12A and 12B are graphs explaining algorithm for setting up a threshold value.
Figure 12B:
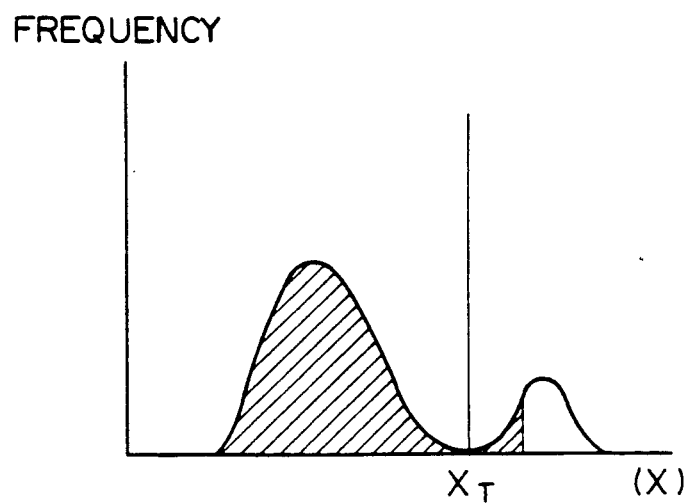

FIG. 11 is a graph exemplifying normal and abnormal waveforms in electrocardiographic waveforms and FIGS. 12A and 12B are graphs explaining algorithm for setting up a threshold value.

In electrocardiographic waveforms shown in FIG. 11, for example, waveforms N1, N2, N3, and N4 are normal waveforms, while waveform V1 is a typical example of an abnormal waveform which indicates an extrasystole associated with the ventricle. In such case, the area A of the QRS portion or the width W of the QRS portion is measured so as to determine on the basis of the measured values thereof whether the electrocardiographic waveforms are normal or abnormal.

However, as described above, in respect of feature values a threshold value between the normality and the abnormality cannot be absolutely determined. It has been well known that the value varies due to individual difference and even for a person the value also changes during a day or between respective examination days. Further, there is a case capable of clearly separating an electrocardiographic waveform range into a normal range and an abnormal range and another case incapable of doing so. This is a tendency or a phenomenon found in other clinical test values (obtained in a blood type test).

In other words, in a histogram prepared for a feature value X on the basis of electrocardiographic waveforms a normal range N and an abnormal range V can be clearly separated as shown in FIG. 9A. In a histogram prepared for another feature value Y, however, the normal range N and the abnormal range V overlap each other partially on the boundary area as shown in FIG. 9B, which may cause the range unable to be clearly separated. Further, in a histogram prepared for the other feature value Z considerable portions of the normal range N and the abnormal range V overlap each other as shown in FIG. 9C. As mentioned above, a tendency occurred depending on feature values may vary. Still further, even in a histogram prepared for the same feature value X, there may be a case, as mentioned above, that individual difference among subjects causes differences as those shown in FIGS. 9A, 9B, and 9C. In addition, even a histogram prepared with the same feature value for a person may vary, as described above, due to change during a day or between respective examination days like those shown in FIGS. 9A, 9B, and 9C.

As mentioned above, in the case of the histogram shown in FIG. 9A, when a threshold value is fixed on the position XT, the normal waveform N and the abnormal waveform V are correctly separated, resulting in providing highly accurate judgement of normality and abnormality. Further, in the case of the histogram shown in FIG. 9B, separation is not made so clearly as that shown in FIG. 9A, while by fixing a threshold value on the position YT separation and judgement of the normality and the abnormality can be achieved at a certain level of accuracy.

In the case of the histogram shown in FIG. 9A, however, it is recognized that there exist two mountain-shaped distributions clearly separated, while it is impossible to judge which mountain-shaped distribution is normal or abnormal, based only on information given here so far. Thus, to judge which mountain-shaped distribution is normal or abnormal, among feature values a histogram indicating the QRS width W which is considered to be a diagnostic reference for determining normality and abnormality is used. In particular, in this histogram a value 120 mS is regarded as a general boundary value (a threshold value). Consequently, in the case of a distribution as shown in FIG. 12A, 120 mS is used as a threshold value to assume data in a realm having the QRS width not less than 120 mS to be normal and data in a realm having the QRS width less than 120 mS to be abnormal.

It is natural that, as described above, such judging method alone cannot achieve correct judgement like one capable of coping with individual differences and change during a day or between respective examination days. Therefore, data in the realm having the QRS width less than 120 mS considered to be normal data are projected on a histogram, as shown in FIG. 9A, employed and selected in the step 470 as feature values capable of obtaining a higher degree of separation and better judgement. The result is shown in FIG. 12B. By the projection it can be recognized that the data in the realm having the QRS width less than 120 mS correspond with a mountain-shaped distribution on the left side in FIG. 12B as indicated with a shaded portion. Further, though there are a few data as indicated with a shaded portion projected on the right mountain-shaped distribution, it can be recognized that the probability of the normality is extremely high for the left mountain-shaped distribution. Consequently, as it can be judged that the mountain-shaped distribution on the left side of the threshold value XT indicates normal data and the mountain-shaped distribution on the right side thereof indicates abnormal data, by using the threshold value XT for feature values electrocardiographic data in the first analysis section are judged.

In addition, the present invention is not to be restricted by those embodiments previously described but can be transformed into various shapes. In the illustrative embodiments described above, for example, a long-term electrocardiographic measurement is explained, while it is useless to say that the present invention is also applicable to a long-term measurement, collection and analysis of other signals of a living body, such as blood pressure waveforms, brain waveforms, etc., without being limited to an electrocardiogram. When there exist at the time of selecting and extracting feature values two or more histograms for feature values having a similar high degree of separation, a judgement may be individually made for the respective feature values and, when any value judged to be abnormal exists therein, the waveform may be judged to be abnormal. In this way, a detecting sensitivity of abnormal waveforms can be improved. In order to further improve the sensitivity, a judgement is executed by a histogram in the step 450, and when even electrocardiographic data judged to be normal in the step 450 are judged to be abnormal by a judgement of the R—R interval in the step 455, the final judgement may adopt a method of judging the data to be abnormal.

Also, in the previous paragraph there is described a case of independently establishing a histogram preparation section and a histogram analysis section and making the former longer than the latter as shown in FIG. 10 to carryout parallel processing of preparation of histograms, while both sections may be established in the same length so as to repeat preparation of histograms by means of serial processing, or a modification may be made to a histogram just before preparation of a histogram shown in FIG. 10 to process preparation of histograms.

As clearly understood from the above description, in accordance with the present invention, when a long-term vital signal measurement is effected, for example, in a long-term electrocardiographic measurement, histograms of a plurality of feature values for measured electrocardiographic waveforms are prepared in the first predetermined period of time and then on a plurality of the histograms features values having the best shape of separation are selected. Consequently, when those selected feature values are used for a judgement of normality and abnormality of electrocardiographic waveforms after the first predetermined period of time, an accurate judgement can be achieved without any influence caused by individual difference and other variable factors. Yet, by executing the processing repetitively it is possible to automatically detect abnormal electrocardiographic waveforms while measuring an electrocardiogram, and as a result, without being affected by individual difference in electrocardiographic waveforms, or change in a person during a day or between respective examination days an accurate detection of abnormal electrocardiographic waveforms can be achieved.

In accordance with the present invention, the vital signal measuring apparatus, when a histogram forming means prepares histograms of a plurality of feature values associated with vital signals, causes a feature value selecting means to select on the basis of a distribution of the histograms feature values having information most useful to a vital signal analysis, thereby can effect an vital signal analysis by an analizing means with considerations of the individual characteristics of subjects. Yet, when a histogram is prepared in the unit of a predetermined period of time, accurate judgement and analysis of normality and abnormality in response to changes in a person during a day or between respective examination days can be achieved, and abnormal signals of the living body can be easily selected to be stored in a memory.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

What is claimed is:

1. An apparatus for analyzing vital signals captured from a subject, said apparatus comprising:
    histogram forming means for receiving vital signals and forming different histograms based upon received vital signals with each formed histogram indicating a different feature of the received vital signals;
    selecting means for selecting a selected vital signal feature which is most useful for analysis of the received vital signals based upon histogram distributions provided in the histograms formed by the histogram forming means; and
    analyzing means, responsive to selection of one of the vital signal features as the selected feature by the selecting means, for analyzing the received vital signals on the basis of the selected feature to determine whether or not the received vital signals are normal.

2. An apparatus in accordance with claim 1, wherein the histogram forming means forms the histograms corresponding to the received vital signals during a predetermined period of time.

3. An apparatus in accordance with claim 2, wherein the histogram forming means forms the histograms corresponding to the vital signals captured during a most recent predetermined period of time.

4. An apparatus in accordance with claim 1 further comprising memory means connected to the analyzing means for storing received vital signals that are determined to be abnormal by the analyzing means.

5. An apparatus in accordance with claim 4 further comprising:
    a portable casing for enclosing the histogram forming means, the selecting means, the analyzing means and the memory means; and
    output means housed in the casing and connectable to a utility circuit for reproducing the vital signals stored in the memory means while connected to the utility circuit.

6. An apparatus in accordance with claim 1, wherein the selecting means selects the selected feature based upon which histogram distributions are best separated.

7. An apparatus in accordance with claim 6, wherein the analyzing means determines a threshold value based upon which histogram distributions are best separated, and wherein the analyzing means determines whether or not the received vital signals are normal based upon the selected feature and the threshold value.

8. An apparatus in accordance with claim 1 further comprising input means for receiving electrocardiographic signals as the received vital signals and supplying the histogram forming means with the electrocardiographic signals, the selecting means selecting the selected feature based upon an area of a QRS portion of the electrocardiographic signals, or a width of the QRS portion of the electrocardiographic signals, or upon a height of a peak of an R wave of the electrocardiographic signals.

9. A method of analyzing vital signals captured from a subject comprising the steps of:
    receiving the vital signals from the subject;
    forming different histograms based upon the vital signals with each formed histogram indicating a different feature of the vital signals;
    selecting a selected feature which is most useful for an analysis of the vital signals based upon histogram distributions provided by the histograms; and
    analyzing the vital signals on the basis of the selected feature to determine whether or not the vital signals are normal.

10. A method in accordance with claim 9, wherein in said step of forming the histograms, the histograms are formed on the basis of the vital signals captured during a predetermined period of time.

11. A method in accordance with claim 10, wherein in said step of forming the histograms, the histograms are formed on the basis of the vital signals captured during a most recent predetermined period of time.

12. A method in accordance with claim 9 further comprising the step of storing the vital signals determined to be abnormal in a memory.

13. A method in accordance with claim 9, wherein, in said selecting step, of the selected feature is selected based upon which histogram distributions are best separated.

14. A method in accordance with claim 13 further comprising the steps of determining a threshold value based upon which histogram distributions are best separable, and determining whether or not the vital signals are normal based upon the selected feature and the threshold value.

15. A method in accordance with claim 9 further comprising the step of receiving electrocardiographic signals as the vital signals, and wherein, in said selecting step, the selected feature is selected based upon an area of a QRS portion of the electrocardiographic signals or a width of the QRS portion, or a height of a peak of an R wave of the electrocardiographic signals.

* * * * *